United States Patent
Shelton et al.

(10) Patent No.: US 12,324,888 B2
(45) Date of Patent: Jun. 10, 2025

(54) URETERAL STENT WITH ANTI-MIGRATION FEATURES

(71) Applicant: GYRUS ACMI, INC., Southborough, MA (US)

(72) Inventors: Kurt G. Shelton, Woburn, MA (US); Antonio E. Prats, Shrewsbury, MA (US)

(73) Assignee: GYRUS ACMI, INC., Southborough, MA (US)

( * ) Notice: Subject to any disclaimer, the term of this patent is extended or adjusted under 35 U.S.C. 154(b) by 1152 days.

(21) Appl. No.: 17/071,143

(22) Filed: Oct. 15, 2020

(65) Prior Publication Data

US 2021/0023350 A1  Jan. 28, 2021

Related U.S. Application Data

(63) Continuation of application No. 15/869,962, filed on Jan. 12, 2018, now Pat. No. 10,857,337, which is a continuation of application No. 15/200,134, filed on Jul. 1, 2016, now Pat. No. 9,937,031, which is a continuation of application No. 14/643,573, filed on Mar. 10, 2015, now Pat. No. 9,409,002.

(60) Provisional application No. 61/975,151, filed on Apr. 4, 2014.

(51) Int. Cl.
*A61M 27/00* (2006.01)
*A61F 2/04* (2013.01)

(52) U.S. Cl.
CPC .............. *A61M 27/008* (2013.01); *A61F 2/04* (2013.01); *A61M 27/002* (2013.01); *A61F 2002/048* (2013.01)

(58) Field of Classification Search
CPC .............. A61M 27/008; A61M 27/002; A61M 2002/048; A61F 2/04
See application file for complete search history.

(56) References Cited

U.S. PATENT DOCUMENTS

| 3,938,529 A | * | 2/1976 | Gibbons | .............. A61M 27/008 |
| | | | | 604/524 |
| 4,990,133 A | | 2/1991 | Solazzo | |
| 5,141,502 A | | 8/1992 | Macaluso, Jr. | |

(Continued)

FOREIGN PATENT DOCUMENTS

| CN | 202235790 U | 5/2012 |
| CN | 102579171 A | 7/2012 |

(Continued)

OTHER PUBLICATIONS

S.M. Tillem and A.D. Smith, Edited by D. Yachia; "Stenting after endopyelotomy"; 2011, ISIS Medical Media; pp. 191-199.

(Continued)

*Primary Examiner* — Philip R Wiest
(74) *Attorney, Agent, or Firm* — Oliff PLC

(57) ABSTRACT

A ureteral stent including a tubular body and a first anti-migration feature including one or more projections extending outward from the tubular body. The first anti-migration feature may be configured to be placed entirely within a patient's ureter. The first anti-migration feature may be provided entirely at a proximal bladder section of the tubular body and be configured to not enter the patient's bladder.

12 Claims, 13 Drawing Sheets

(56) References Cited

U.S. PATENT DOCUMENTS

| | | | |
|---|---|---|---|
| 5,176,626 A * | 1/1993 | Soehendra | A61F 2/94 604/9 |
| 5,769,821 A | 6/1998 | Abrahamson et al. | |
| 6,395,021 B1 * | 5/2002 | Hart | A61F 2/82 623/1.2 |
| 6,709,465 B2 * | 3/2004 | Mitchell | A61F 2/94 606/127 |
| 7,476,256 B2 | 1/2009 | Meade et al. | |
| 7,731,676 B2 * | 6/2010 | Maeda | A61M 27/008 606/127 |
| 8,366,673 B2 | 2/2013 | Reydel | |
| 8,377,041 B2 | 2/2013 | Frassica et al. | |
| 9,409,002 B2 * | 8/2016 | Shelton | A61F 2/04 |
| 9,937,031 B2 | 4/2018 | Shelton et al. | |
| 10,857,337 B2 * | 12/2020 | Shelton | A61F 2/04 |
| 2001/0021835 A1 | 9/2001 | Mitchell et al. | |
| 2003/0171708 A1 * | 9/2003 | Segura | A61M 27/008 604/8 |
| 2003/0176831 A1 | 9/2003 | Gellman et al. | |
| 2003/0195456 A1 | 10/2003 | Robertson | |
| 2007/0112437 A1 | 5/2007 | Shank | |
| 2012/0089236 A1 | 4/2012 | Errico et al. | |

FOREIGN PATENT DOCUMENTS

| | | |
|---|---|---|
| CN | 102791316 A | 11/2012 |
| JP | 2013-052304 A | 3/2013 |
| WO | 97/25090 A1 | 7/1997 |
| WO | 99/09911 A2 | 3/1999 |

OTHER PUBLICATIONS

Jun. 9, 2015 International Search Report with Written Opinion in PCT/US2015/019590.
Feb. 23, 2016 Office Action issued in U.S. Appl. No. 14/643,573.
Oct. 4, 2016 International Preliminary Report on Patentability issued in International Application No. PCT/US2015/019590.
Jan. 27, 2017 Office Action issued in U.S. Appl. No. 15/200,134.
Mar. 3, 2017 Office Action issued in Chinese Patent Application No. 201580003251.8.
Sep. 7, 2017 Office Action issued in U.S. Appl. No. 15/200,134.
U.S. Appl. No. 14/643,573, filed Mar. 10, 2015 in the name of Shelton et al.
U.S. Appl. No. 15/200,134, filed Jul. 1, 2016 in the name of Shelton et al.

* cited by examiner

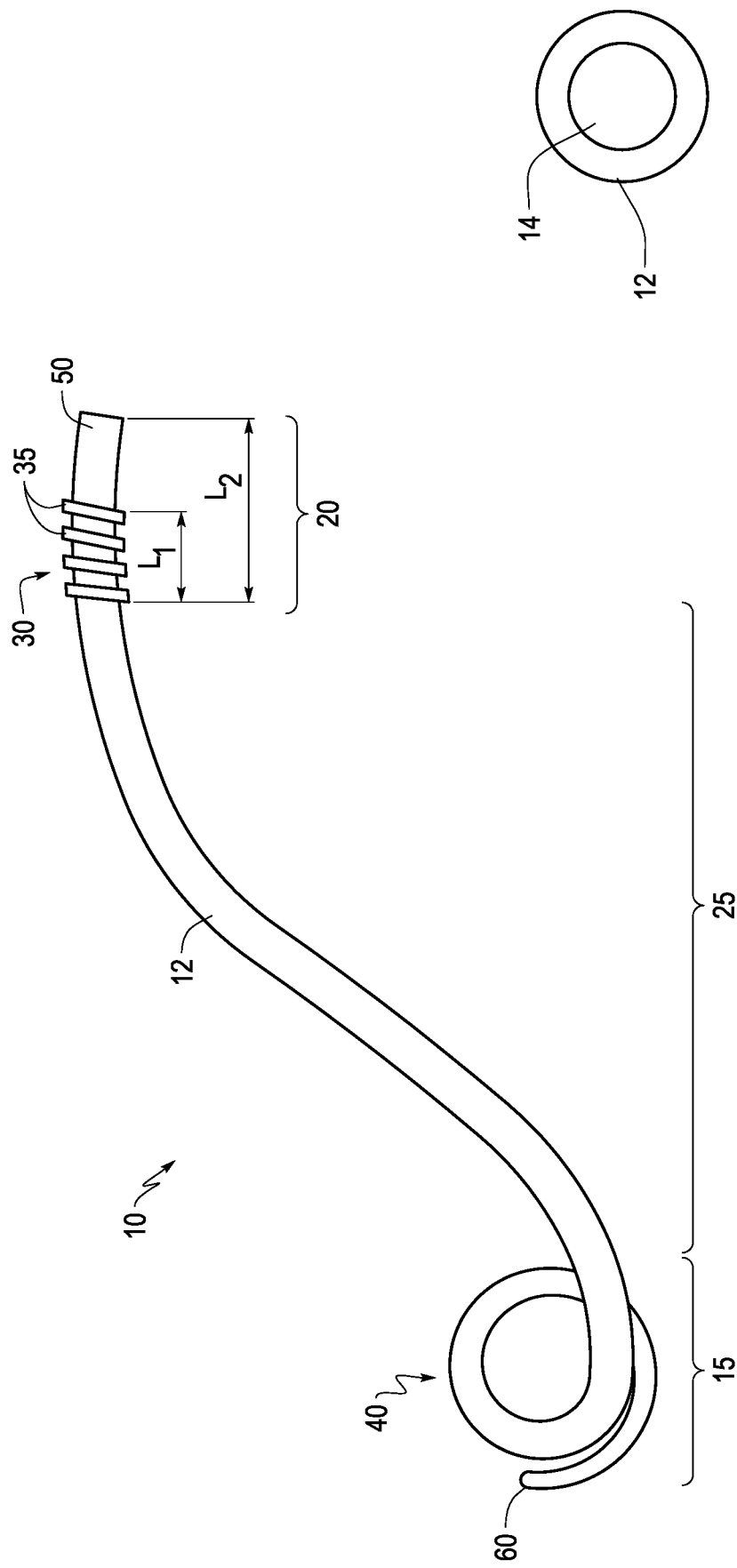

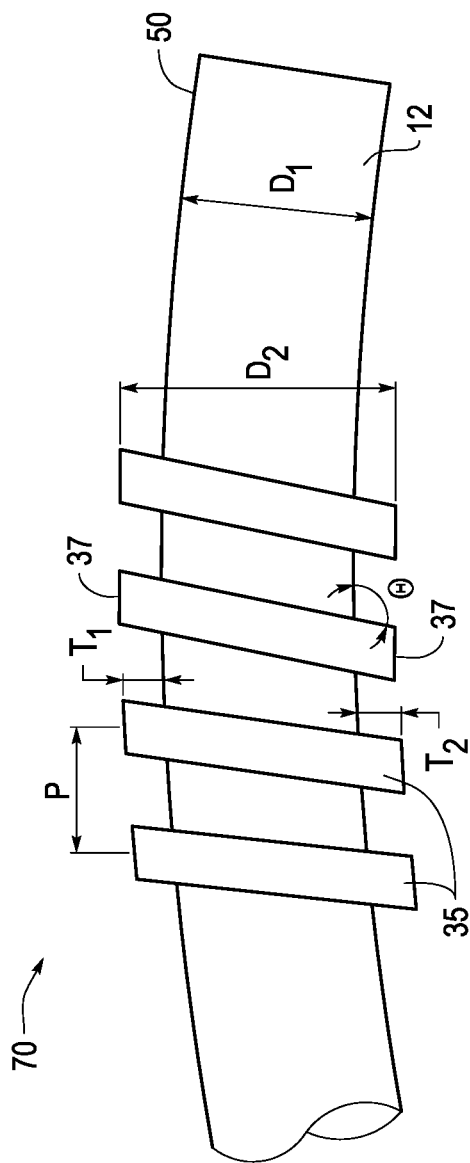
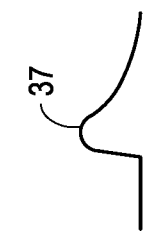
FIG. 2F
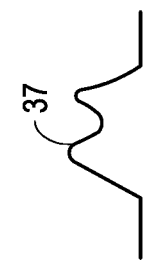
FIG. 2E
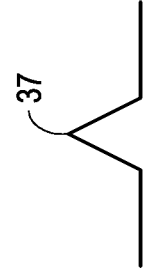
FIG. 2D
FIG. 2A
FIG. 2C
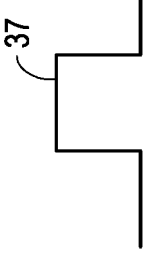
FIG. 2B

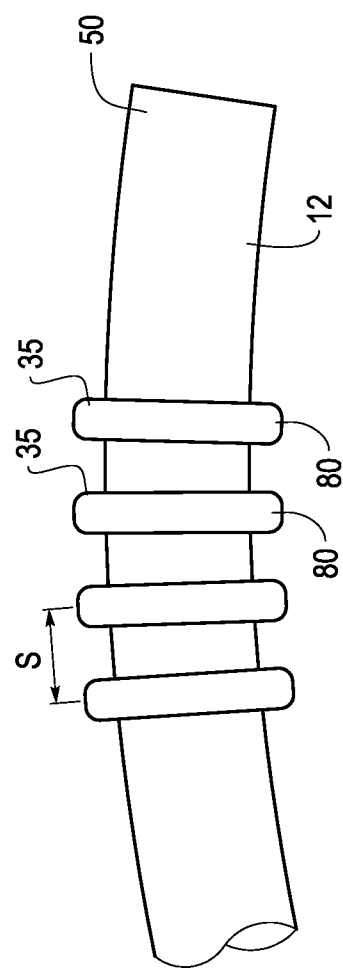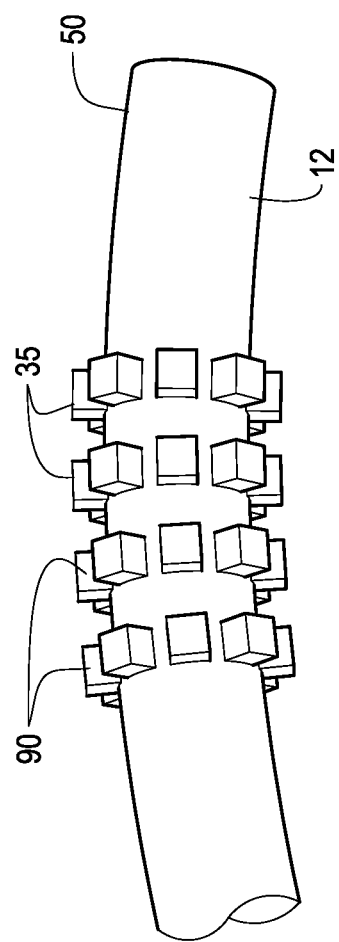

URETERAL STENT WITH ANTI-MIGRATION FEATURES

CROSS-REFERENCE TO RELATED APPLICATIONS

This application is a continuation of application Ser. No. 15/869,962 filed Jan. 12, 2018, which in turn is a continuation of application Ser. No. 15/200,134, filed Jul. 1, 2016 (issued as U.S. Pat. No. 9,937,031 on Apr. 10, 2018), which in turn is a continuation of U.S. application Ser. No. 14/643,573, filed Mar. 10, 2015 (issued as U.S. Pat. No. 9,409,002 on Aug. 9, 2016), and which claims the benefit of U.S. Provisional Application No. 61/975,151, filed Apr. 4, 2014. The disclosure of the prior applications is hereby incorporated by reference herein in its entirety.

BACKGROUND

The invention relates to ureteral stents.

A ureter is a tubular passageway in the body that conveys urine from a kidney to a bladder. Ureteral stents are used to facilitate urinary drainage from the kidney to the bladder in patients having a ureteral obstruction or injury, or to protect the integrity of the ureter in a variety of surgical manipulations. Ureteral stents are typically about 30 cm long, hollow catheter-like devices made from a polymer and placed within the ureter with the distal end residing in the kidney and the proximal end residing in the bladder. Ureteral stents function by channeling the flow of urine from the kidney to the bladder. One or both ends of a ureteral stent may be coiled in a pigtail shape to prevent the upward and/or downward migration of the stent due to patient movement. For example, the ureter may stretch up to 5 cm in either direction during a patient's normal bodily movements, such as movement during breathing. If the stent is not sufficiently anchored, this may result in stent migration and displacement.

Another factor to be considered relates to tissue irritation caused by the stent. A stent may cause tissue irritation due to the relative movement between the stent and the ureter during natural stretching of the ureter, even when the stent is properly anchored. A typical semi-rigid, anchored stent is unable to adjust for the natural extension and contraction of the ureter during bodily movements, resulting in pressure and irritation of the ureter and surrounding tissue.

Regions of tissue most vulnerable to stent-induced irritation include the kidney, the renal pelvis, the sensitive bladder tissue in the trigonal region, and tissue of the ureteral vesicle junction leading into the bladder. Irritation may be caused by the static or dynamic contact of the semi-rigid stent with sensitive tissues of the body, such as the kidney and the renal pelvis. Chronic trigonal tissue irritation may result from contact of tissue by the bladder-anchoring features of the stent, for example, pigtails at the stent ends. Irritation problems are of concern regardless of the duration of use of the stent. Irritation is of particular concern, however, when use of a stent is required over a long time period.

Another problem associated with ureteral stents is urine reflux and pain during urine voiding. On the initiation of voiding, the bladder wall muscles contract causing the pressure inside the bladder to increase. Because a typical ureteral stent holds the ureteral orifice open, increased bladder pressure during voiding is transmitted to the kidney through the stent, causing urine reflux and flank pain.

SUMMARY

Many factors thus should be considered when designing a ureteral stent. Such factors include the function to be performed by different parts of the stent, such as anchoring, maintenance of an open-flow condition, etc., and comfort. In particular, it is desirable to make a ureteral stent that is easy to insert, comfortable at all times, exhibits good coil recovery (the tendency of the stent ends to return to the originally-designed coiled state after having been straightened, for example, during insertion), remains anchored during normal bodily movements, provides for suitable flow of urine, is easily removable and avoids fracture during insertion, use and removal. The invention relates to various designs for a ureteral stent that facilitate some or all of the above goals.

Ureteral stents according to embodiments of the invention may include a tubular body defining a lumen and having (i) a distal kidney section to be placed in or near a patient's kidney, (ii) a proximal bladder section to be placed within or near the patient's bladder, and (iii) a ureter section between the distal and proximal sections to be placed within the patient's ureter. A first anti-migration feature may be provided at the proximal bladder section and may include one or more projections extending outward from the tubular body. The first anti-migration feature may extend less than a total length of the proximal bladder section, and may be configured to not enter the patient's bladder. Furthermore, a second anti-migration feature may be provided at the distal kidney section, the proximal bladder section, or both.

The invention also relates to methods for providing drainage from a kidney to a bladder within a patient in a ureteral stent. The methods may include deploying the ureteral stent from an outer sheath within a ureter of a patient and sliding an outer layer of the ureteral stent from a first position to a second position to expose one or more projections on the ureteral stent such that the one or more projections move from a delivery position in which the projections do not protrude beyond an outer circumference of the tubular body, to a deployment position in which the projections protrude beyond the outer circumference of the tubular body and contact a ureteral wall of the patient. Additionally, the methods may include locking the position of the outer layer with regard to the tubular body to lock the projections in the deployment position.

BRIEF DESCRIPTION OF THE DRAWINGS

Various exemplary embodiments of ureteral stents according to aspects of the invention will be described in detail with reference to the following drawings in which:

FIGS. 1A-1C show ureteral stents according to embodiments of the invention;

FIGS. 2A-2F show ureteral stents according to embodiments of the invention;

FIG. 3 shows an anti-migration feature of a ureteral stent according to embodiments of the invention;

FIG. 4 shows an anti-migration feature of a ureteral stent according to embodiments of the invention;

DETAILED DESCRIPTION OF EMBODIMENTS

Figure 1C:
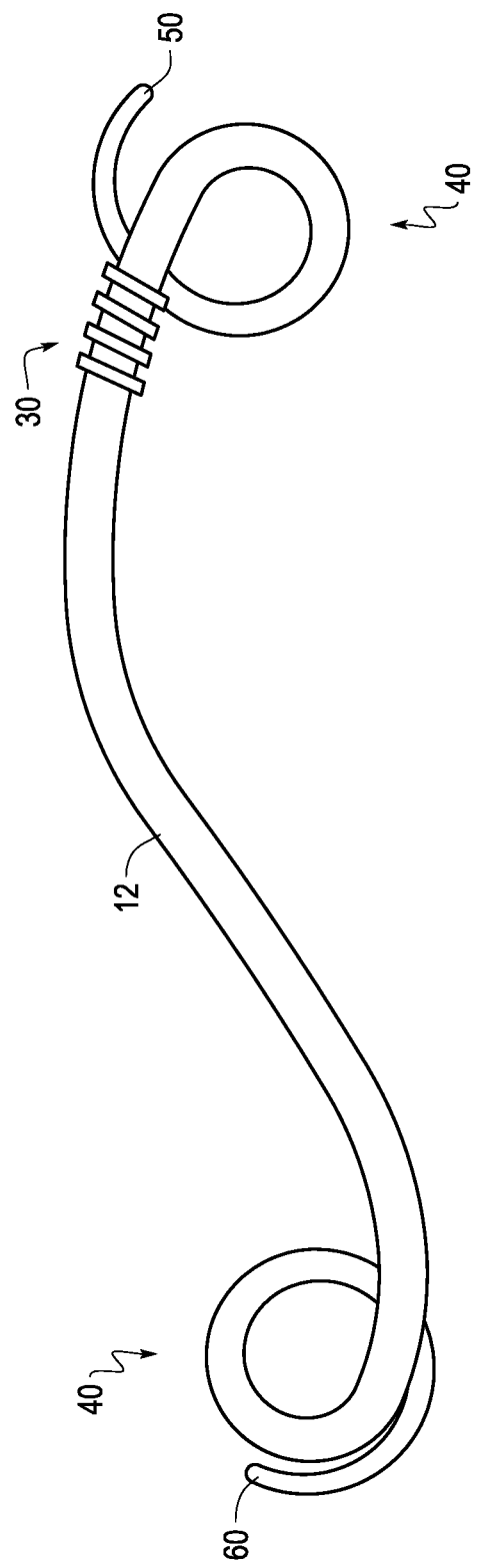

The disclosure relates to ureteral stents configured to reduce movement of the stent when deployed within a patient. As shown in FIG. 1A, ureteral stent 10 may include a tubular body 12 having a proximal bladder section 20, a distal kidney section 15, and a ureter section 25. The proximal bladder section 20 may be disposed at the proximal end 50 of tubular body 12, and may be configured to be disposed in or near a patient's bladder. The distal kidney section 15 may be disposed at the distal end 60 of tubular body 12, and may be configured to be disposed in or near the patient's kidney. As further shown in FIG. 1A, the ureter section 25 may be disposed between the proximal bladder section 20 and the distal kidney section 15, and may be configured to be disposed within a patient's ureter.

Tubular body 12 may define a lumen 14 configured for the flow of fluid from the distal end 60 to the proximal end 50. The lumen 14 may be of constant diameter throughout the length of tubular body 12 (FIG. 1B). However, it is further contemplated that the lumen 14 may have varying diameters along the length of tubular body 12. For example, the lumen 14 may have a relatively larger diameter at distal end 60 and a relatively smaller diameter at proximal end 50. Alternatively, the lumen 14 may have a relatively larger diameter at proximal end 50 and a relatively smaller diameter at distal end 60. Furthermore, the lumen 14 may include various cross-sectional configurations, for example, such as circular, square, etc. As is well known in the art, distal and proximal ends 60, 50 can be open. Alternatively or additionally, the distal and proximal ends 60, 50 can include perforations. Proximal end 50 may not extend through the ureteral orifice, and it may be made of a soft, flexible material like silicone or other flexible, bacterial-resistant material to reduce transverse forces on the bladder anatomy when the patient bends.

A first anti-migration feature 30 may be provided at the proximal bladder section 20, and a second anti-migration feature 40 may be provided at the distal kidney section 15, the proximal bladder section 20, or both. The first anti-migration feature 30 may be located at a portion of the longitudinal length of the tubular body such that the first anti-migration feature 30 is configured to not enter a patient's bladder when the ureteral stent 10 is deployed with the patient. Therefore, for example, the first anti-migration feature 30 may be configured to not enter the patient's bladder when the proximal end 50 of the proximal bladder section 20 is positioned within or near the patient's bladder. In some embodiments, the first anti-migration feature 30 may extend less than an entirety of a longitudinal length of the proximal bladder section 20, as shown in FIG. 1A. For example, the first anti-migration feature 30 may extend for ¾, ⅔, ½, or ⅓ the length of the proximal bladder section 20. Preferably, the proximal-most end of the first anti-migration feature 30 is spaced from (distally spaced from) the proximal end 50 of the proximal bladder section 20. As shown in the embodiment of FIG. 1A, the first anti-migration feature extends a length $L_1$ and the proximal bladder section 20 extends a length $L_2$, wherein $L_1$ is approximately ½ the length of $L_2$. The length of $L_2$ within the proximal bladder section is selected to provide sufficient anti-migration friction to counteract the natural peristaltic action of the ureter. In a preferred embodiment, the anti-migration feature 30 locally increases the effective outer diameter of proximal bladder section 20 by at least 20-50% over a length of approximately 3 cm. A more substantial increase in diameter (i.e. 50-70%) can support a shorter anti-migration length ($L_1$). In some embodiments, the first anti-migration feature 30 extends approximately the entire length of the proximal bladder section 20 such that $L_1$ is approximately equal to $L_2$.

The first and second anti-migration features 30, 40 may collectively reduce substantial migration of the ureteral stent 10. For example, the first anti-migration feature 30 may reduce retrograde movement of the ureteral stent 10 (i.e., movement distally and away from the patient's bladder), when the ureteral stent 10 is disposed within a patient. Additionally, the second anti-migration feature 40 may reduce antegrade movement of the ureteral stent 10 (i.e. movement proximally and toward the patient's bladder). In some embodiments, the first and second anti-migration features 30, 40 may prevent such movement of the ureteral stent 10. It is further contemplated that the ureteral stent 10 may include only the first anti-migration feature 30 or the second anti-migration feature 40 to reduce and/or prevent such movement of the ureteral stent 10.

In some embodiments, the ureteral stent 10 may include the second anti-migration feature 40 at both the proximal end 50 and distal end 60 (FIG. 1C). In this embodiment, the second anti-migration feature 40 at the proximal end 50 may further reduce and/or prevent retrograde movement of the ureteral stent 10. For example, the second anti-migration feature 40 at the proximal end 50 may be configured to extend into the patient's bladder. In some embodiments, the second anti-migration feature 40 may be provided at only the proximal end 50 of the ureteral stent 10.

The second anti-migration feature 40, as described in further detail below, may alternatively refer to one or more features selected from a list including: a mesh structure configured to expand outward when released from an outer sheath and a cross-sectional contouring provided to the first anti-migration feature 30.

The first anti-migration features 30 may be one or more projections 35 extending radially outward away from an outermost surface of the tubular body 12. As shown in FIG. 2A, the protrusions 35 may include a radially outermost leading edge 37. An outermost diameter $D_1$ of the tubular body 12 may be less than an outermost diameter $D_2$ of the radially outermost leading edge 37. The diameter $D_2$ may be, for example, 1.0-3.0 times larger than the diameter $D_1$. In some embodiments, the diameter $D_2$ may be 1.2 to 1.5 times larger than diameter $D_1$, and for example, 1.3 times larger.

As shown in FIG. 2A, the projections 35 may extend a distance $T_1$ from a top surface of the tubular body 12, and the projections 35 may extend a distance $T_2$ from a bottom surface of the tubular body 12. Distance $T_1$ may be equal to, larger than, or smaller than $T_2$ such that the radially outermost leading edge 37 may be constant or of varying dimensions along tubular body 12. As shown in FIG. 2A, $T_1$ and $T_2$ are approximately equal. It is further contemplated that the radially outermost leading edge 37 may comprise varying shapes. For example, when viewed in cross-section, leading edge 37 may form a rounded configuration (FIG. 2B), a square configuration (FIG. 2C), a triangular configuration (FIG. 2D), a U-shape configuration (FIG. 2E), and/or a wave configuration (FIG. 2F). Additionally or alternatively, the leading edge 37 may include a chamfered surface. One or more projections 35 may include a leading edge 37 with configurations different from one or more other projections 35 on tubular body 12. For example, half of the projections 35 closer to proximal end 50 may comprise a leading edge 37 with a square configuration (FIG. 2C) and half of the projections 35 closer to the distal end 60 may comprise a leading edge 37 with a rounded configuration (FIG. 2B). In some embodiments, the second anti-migration feature 40 may be provided as a shape contouring to the first anti-migration feature 30. For example, the second anti-migration feature 40 may include shapes as shown in FIGS. 2B-2F that contour to the first anti-migration feature 30.

The projections 35 may form a spiral 70, as shown in FIG. 2A, such that the spiral 70 forms one continuous helical structure along a predefined length of tubular body 12. In some embodiments, spiral 70 may include two or more helical segments, wherein each helical segment forms a continuous structure along a predefined length of tubular body 12. The spiral 70 may be oriented at an angle Θ with regard to the outermost surface of the tubular body, and may include a pitch P. The angle Θ and/or pitch P may be constant or may vary along the length of tubular body 12. For example, the angle Θ may be relatively larger and the pitch P may be relatively smaller closer to the proximal end 50.

In some embodiments, as shown in FIG. 3, the projections 35 may be one or more rings 80, wherein each ring 80 is separated from an adjacent ring 80 by distance S. The distance S between each ring may be constant or may vary along the length of tubular body 12. For example, S may be smaller closer to the proximal end 50.

In other embodiments, the projections 35 may be one or more pads (protrusions) 90. For example, as shown in FIG. 4, each pad 90 may include a raised structure that is separated from each adjacent pad 90. A plane traversing each pad 90 in a longitudinal direction may traverse at least one other pad, and a plane traversing each pad in a crosswise direction, perpendicular to the longitudinal direction, may traverse at least one other pad. The pads 90 may each comprise approximately equal surface areas, or the pads 90 may comprise varying surface areas. For example, the pads 90 closer to the proximal end 50 may comprise relatively larger surface areas. Additionally, the pads 90 may be rigid, and they may be made of the same or of a different material than tubular body 12. In some embodiments, the pads 90 may be made from a different material than the tubular body and include a tacky character such as polyurethane, silicone, or PEBAX (polyether block amide). The pads 90 may be made from the same base material as the tubular body 12, but may be altered to be more tacky. It is contemplated that the pads 90 may further comprise shape contouring as a second anti-migration feature 40, for example as shown in FIGS. 2B-2F. It is further contemplated that the tubular body 12 may include a coating, for example a hydrophilic coating, but that the pads 90 preferably are not coated. This improves the anti-migration function of the pads 90.

According to some embodiments, the first anti-migration feature 30 may be one or more protrusions 100 configured to move from a retracted delivery position (FIG. 5), in which the protrusions 100 do not protrude radially beyond an outer circumference of the tubular body 12, to a protracted deployment position (FIG. 6), in which the protrusions 100 protrude radially outward beyond the outer circumference of the tubular body 12. For example, a slideable outer tube 110 (e.g., outer layer) may be disposed co-axial and outward of the tubular body 12. The outer tube 110 may include one or more apertures 120 through which the protrusions 100 protrude when in the deployment position.

Figure 5:
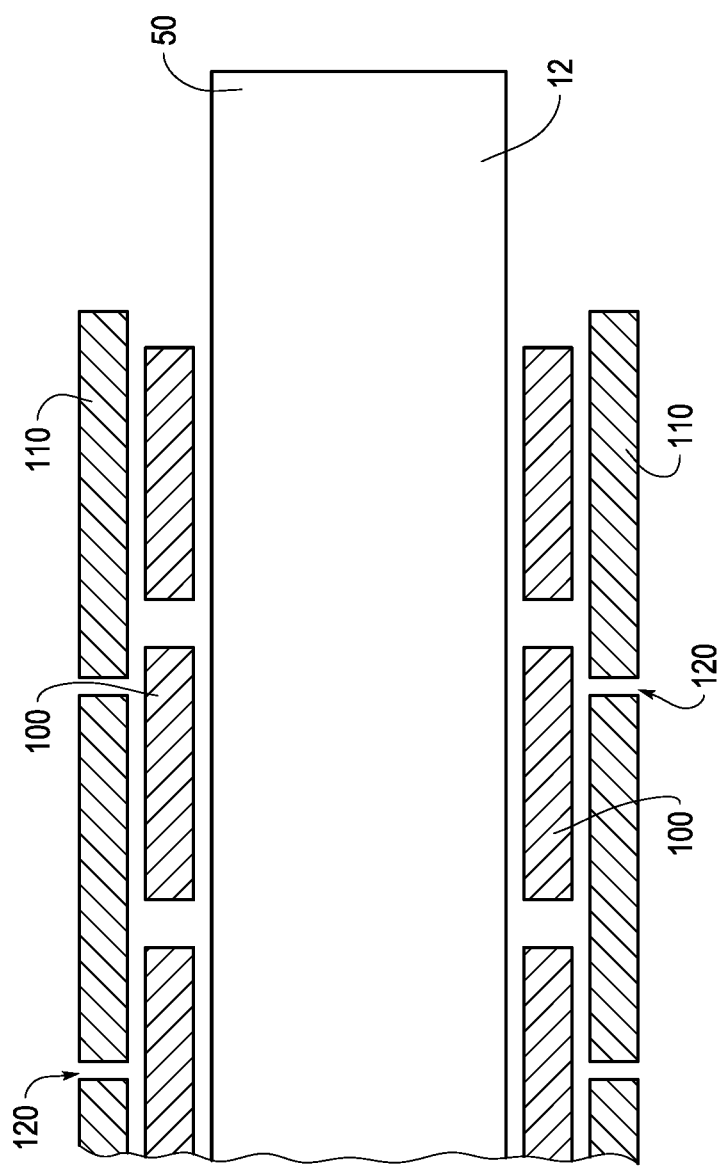
FIG. 5 shows an anti-migration feature of a ureteral stent according to embodiments of the invention.

As shown in FIG. 5, when in the delivery position, the protrusions 100 may be disposed between the outer tube 110 and the tubular body 12. The protrusions 100 may be substantially co-axial with the outer tube 110 and tubular body 12 when the protrusions 100 are in the delivery configuration. The protrusions 100 may be of a spring-like material such that a radially inward force (e.g., toward the tubular body 12) exerted by the outer tube 110 prevents the protrusions from projecting outward when in this delivery position. Movement of the outer tube 110 relative to the protrusions 100 may align the protrusions 100 with apertures 120, disposed on the outer tube 110, such that the protrusions 100 may project through the apertures 120 and assume their delivery position. Therefore, the radially inward force from the outer tube 110 may be removed and the protrusions 100 may assume their delivery position. It is further contemplated that the protrusions 100 may move relative to the outer tube 110 to align the protrusions with the apertures 120.

Figure 6:
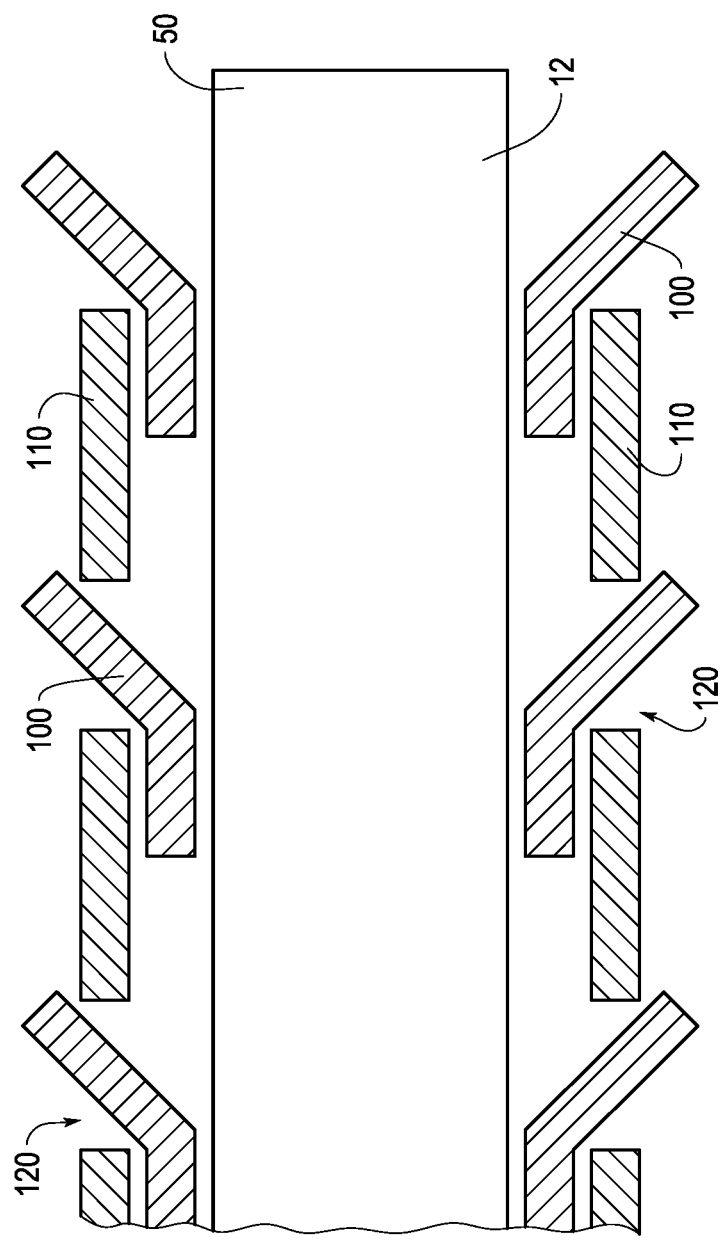
FIG. 6 shows an anti-migration feature of a ureteral stent according to embodiments of the invention.

As shown in FIG. 6, when in the deployment position, a portion of the protrusions 100 may remain disposed between the tubular body 12 and the outer tube 110. This portion of the protrusions 100 may remain secured to the outer tube 12 through any suitable attachment means, such as, for example, a clip, adhesive, screw, thermal coupling, etc.

The protrusions 100 may be deployed and assume their delivery configuration only after the ureteral stent 10 has been delivered to the deployment site within the patient. Therefore, for example, the protrusions 100 may project into ureteral wall tissue of the patient when the protrusions 100 project through apertures 120. This may facilitate securing the ureteral stent 10 within the patient and reducing/preventing retrograde movement of the ureteral stent 10. After the ureteral stent 10 is no longer needed and with the protrusions 100 still deployed, the ureteral stent 10 may be removed from the patient without retracting the protrusions 100 within the outer tube 110 due to the angle at which the deployed protrusions 100 extend. Therefore, the protrusions 100 may remain deployed, and thus in their deployment position, when the ureteral stent 10 is removed from the patient. In other embodiments, the outer tube 110 may be moved relative to the protrusions 100 to fully retract the protrusions 100 within the outer tube 110 (FIG. 5) before the ureteral stent 10 is removed from the patient.

Figure 7:
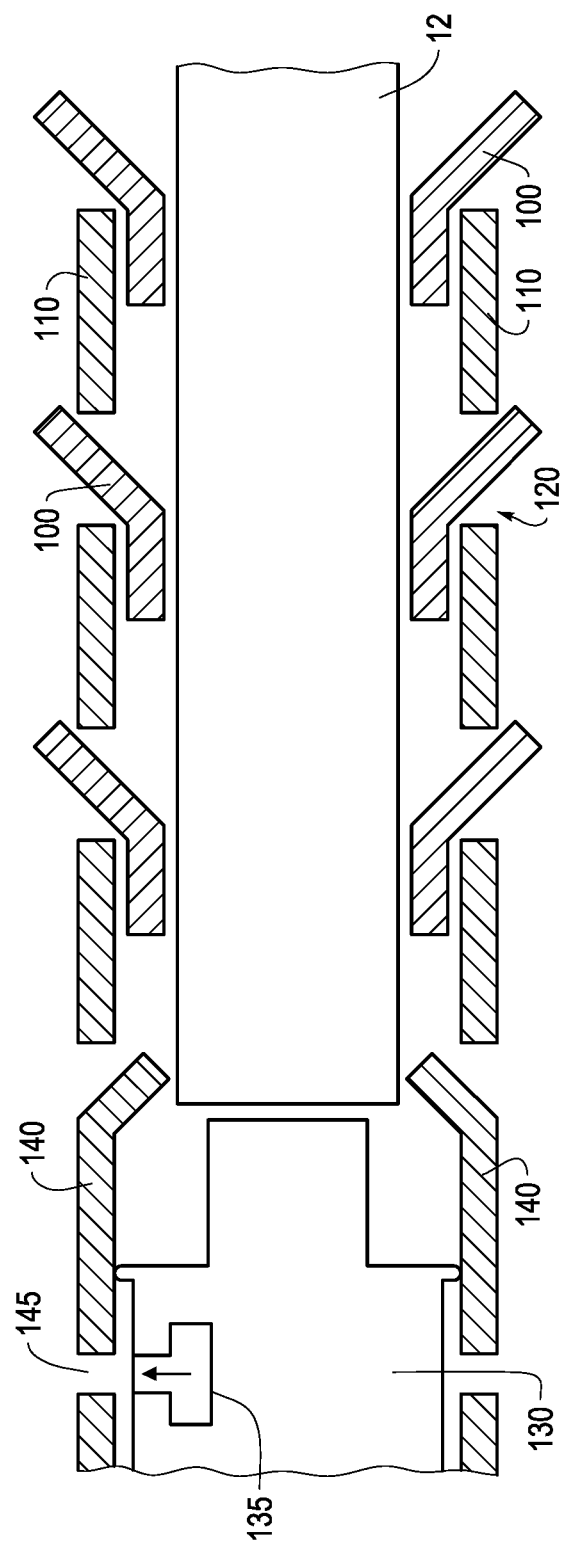
FIG. 7 shows an anti-migration feature of a ureteral stent according to embodiments of the invention.

FIG. 7 shows the ureteral stent of FIGS. 5 and 6 used with an insertion/extraction tool 130. When the ureteral stent 10 is to be inserted into a patient, the insertion/extraction tool 130 is inserted into the proximal end 50 of the stent such that a button (a locking mechanism) 135 that is spring-biased radially outward fits into an opening (hole) 145 in the outer tube 110. The insertion/extraction tool 130 can be used to push and/or pull the ureteral stent 10 into position. For example, when it is desired to deploy the protrusions 100, the insertion/extraction tool 130 may be pulled proximally, which causes the outer tube 110 to move proximally relative to the tubular member 12 and to the protrusions 100. This causes the protrusions 100 to become aligned with the apertures 120 of the outer tube 110, and thereby move from the delivery position to the deployment position shown in FIG. 7. As the outer tube 110 is moved proximally, a slide-lock 140, which is part of the outer tube 110, may move radially inward to the position shown in FIG. 7. Because the slide-lock 140 has moved radially inward, the outer tube 110 cannot be moved distally relative to the tubular body 12. The protrusions 100 thus remain in the deployed position shown in FIG. 7. The button 135 can be moved radially inward so that it no longer extends into the hole 145, and then the insertion/extraction tool 130 can be removed from the ureteral stent 10.

Figure 8:
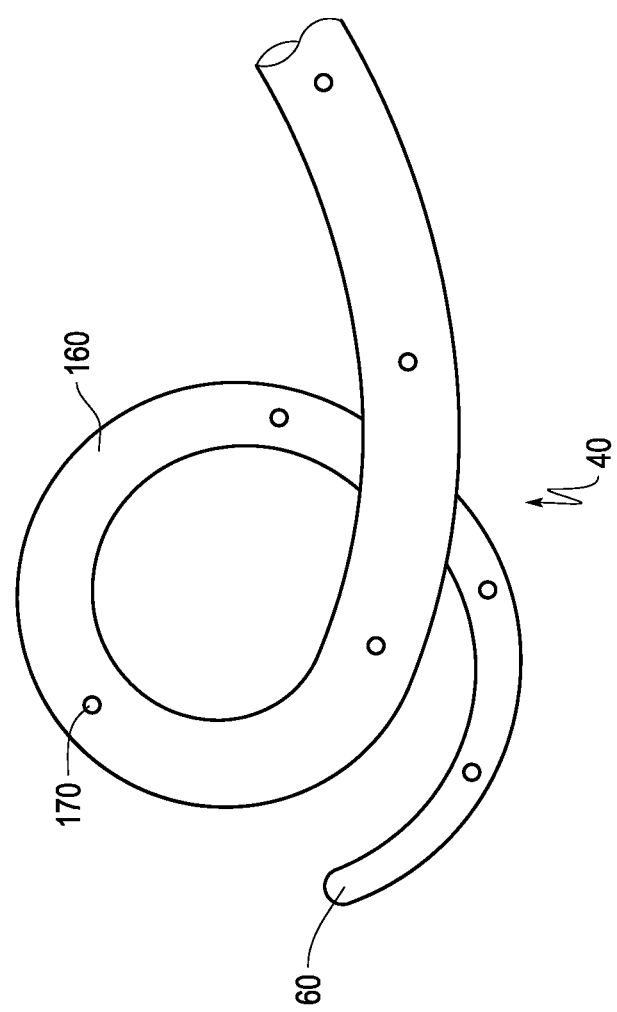
FIG. 8 shows an anti-migration feature of a ureteral stent according to embodiments of the invention.
Figure 14:
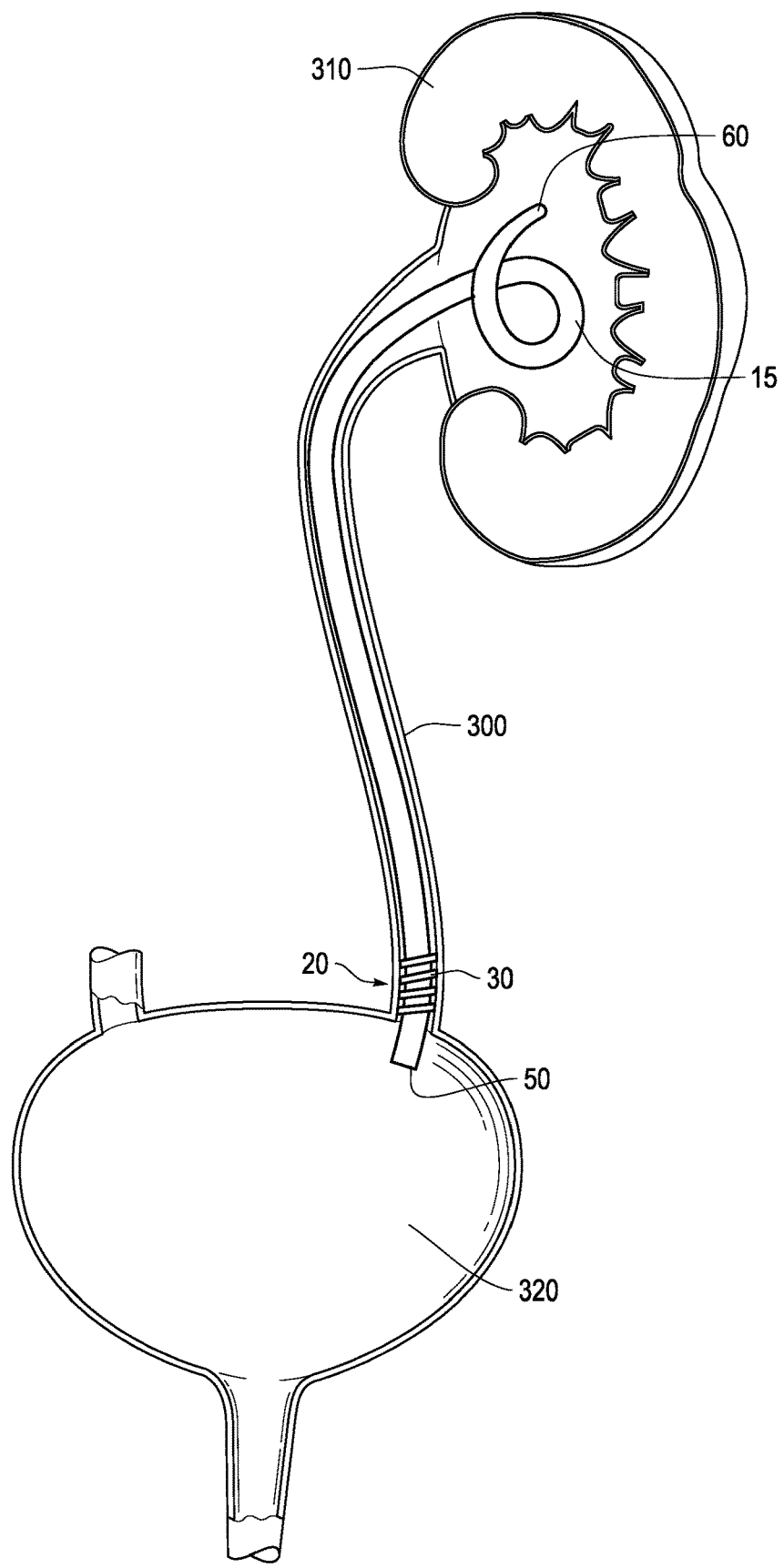
FIG. 14 shows a ureteral stent disposed within a patient's kidney, ureter and bladder.

The second anti-migration feature 40 may include one or more features suitable to reduce and/or prevent antegrade movement of the ureteral stent 10. For example, as shown in FIG. 8, the second anti-migration feature 40 may include a coiled structure 160. As shown in FIGS. 8 and 14, the coiled structure 160 may be configured to longitudinally extend from a tightly coiled state (FIG. 8) to a loosely coiled state (FIG. 14). This extension may be due to movement of the patient, for example when the patient is breathing.

One or more holes 170 may be disposed on the coiled structure 160, and the holes 170 may be of sufficient size for fluid flowing within lumen 14 to exit the tubular body 12. It is further contemplated that the holes 170 are disposed along at least a portion of the proximal bladder section 20 and/or the ureter section 25. For example, the holes 170 may be disposed along the entire length of tubular body 12.

Figure 9A:
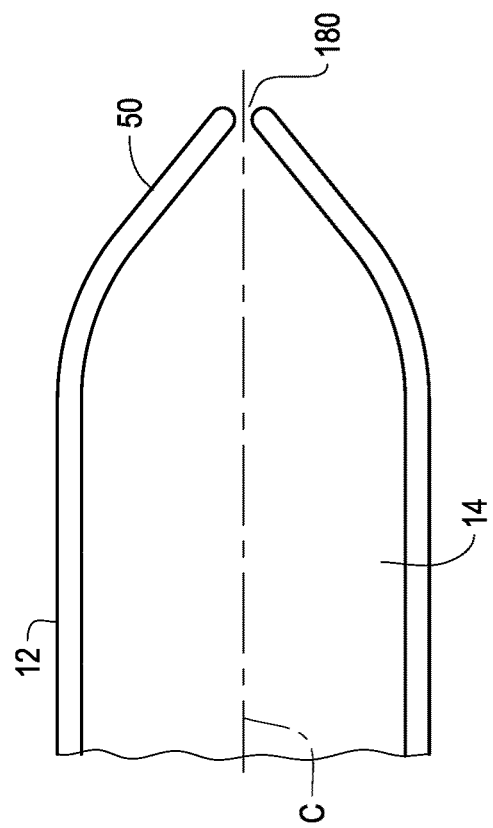
FIGS. 9A and 9B show ureteral stents according to embodiments of the invention.
Figure 9B:
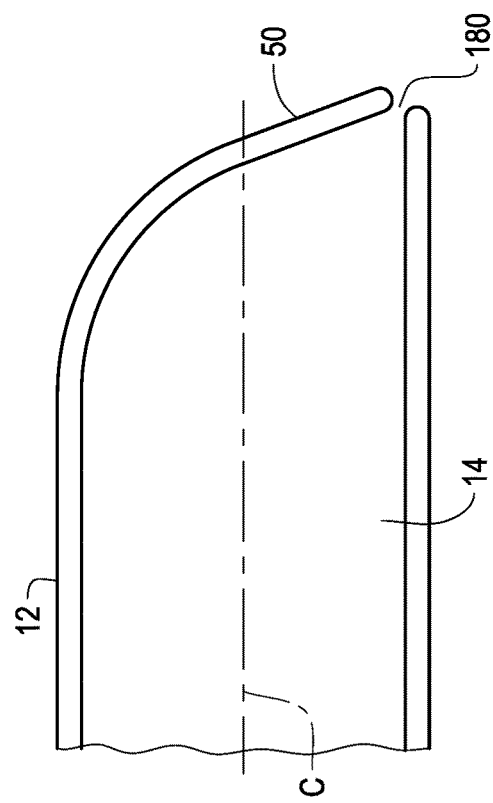

The proximal end 50 of the tubular body 12 may include valve 180. As shown in FIG. 9A the valve 180 may be disposed centrally with regard to a central axis C of the tubular body 12. In other embodiments, as shown in FIG. 9B, the valve may 180 may be disposed lateral to the central axis C of the tubular body 12. The valve 180 may be a one-way valve such that fluid within lumen 14 may only flow out of the lumen 14 via the valve 180, and not into lumen 14 via the valve 180.

Figure 10:
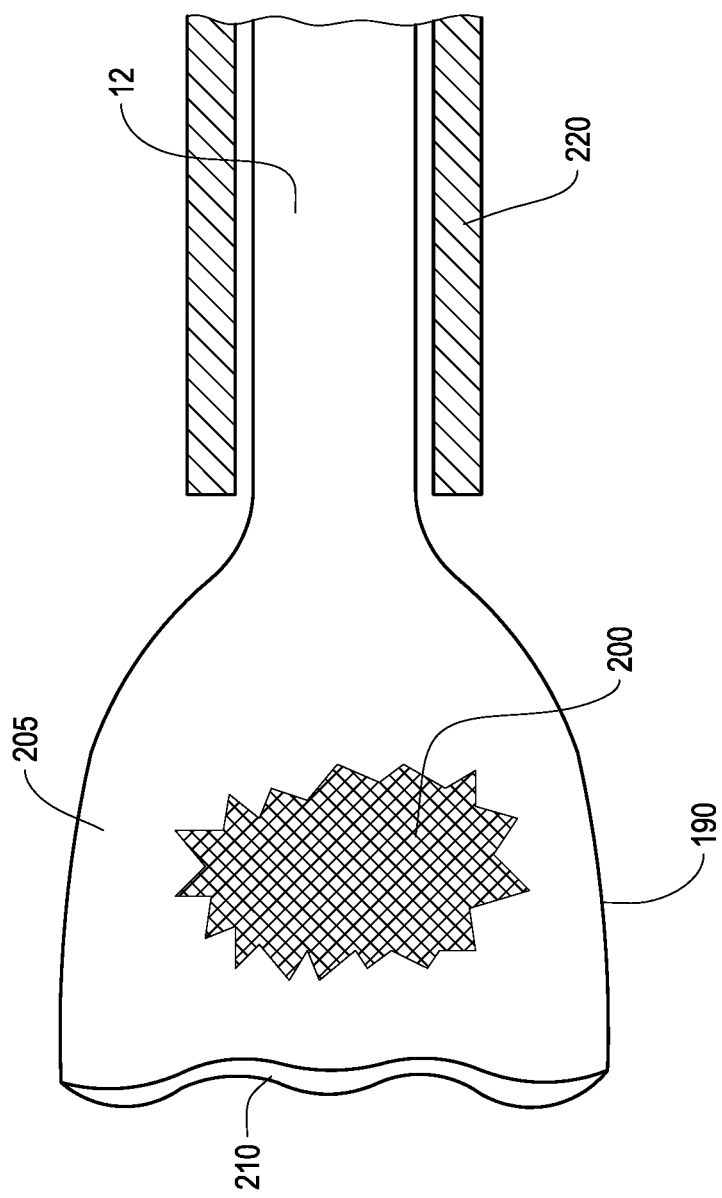
FIG. 10 shows an expandable mesh-like anti-migration feature of a ureteral stent according to embodiments of the invention.

In some embodiments, the second anti-migration feature 40 may include a mesh structure 190 configured to expand outward when released from an outer sheath 220. As shown in FIG. 10, the mesh structure 190 may include a middle mesh layer 200 surrounded by an outer layer 205 and an inner layer 210. The middle mesh layer 200 may be biased to assume an expanded configuration when released from the sheath 220, and the middle mesh layer 200 may be comprised of a network of interlocking struts. The middle mesh layer 200 may include for example, a superelastic alloy such as Nitinol. The outer layer 205 may provide a coating on the mesh layer 200 to reduce friction between the outer sheath 220 and the mesh layer 200. Additionally, the inner layer 210 may provide a coating on the middle mesh layer 200 to facilitate the flow of fluid within the lumen 14. In some embodiments, the outer layer 205 and inner layer 210 may include, for example, a polymeric material. For example, the outer layer 205 may comprise polyurethane, PEBAX (polyether block amide), a low friction polymer including TEFLON (PTFE), FKM (Viton, Fluorel, Aflas), or mixtures thereof. The inner layer 210 may comprise a hydrophilic or polar polymer including, for example, polyurethane or PEBAX (polyether block amide) or mixtures thereof.

Movement of the outer sheath 220 relative to the mesh structure 190 may allow the ureteral stent 10 to move from a delivery position, in which the mesh structure 190 is disposed within the sheath 220, to a deployment position, in which the mesh structure 190 is removed from the sheath 220. As shown in FIG. 10, the mesh structure 190 may expand to a diameter larger than an outer diameter of the remainder of the tubular body 20 when in the deployed position. For example, a mesh coated with a flexible material like silicone may be permitted to expand as shown in FIG. 10. This mesh may be restricted to the distal kidney section 15 of the stent and may have a different cross section than the remainder of the tubular body 12. In another embodiment, mesh structure 190 may be fabricated of the same material as the remainder of the tubular body 12, but with a smaller wall thickness so as to be more flexible to more readily form the second anti-migration feature 40.

Figure 11:
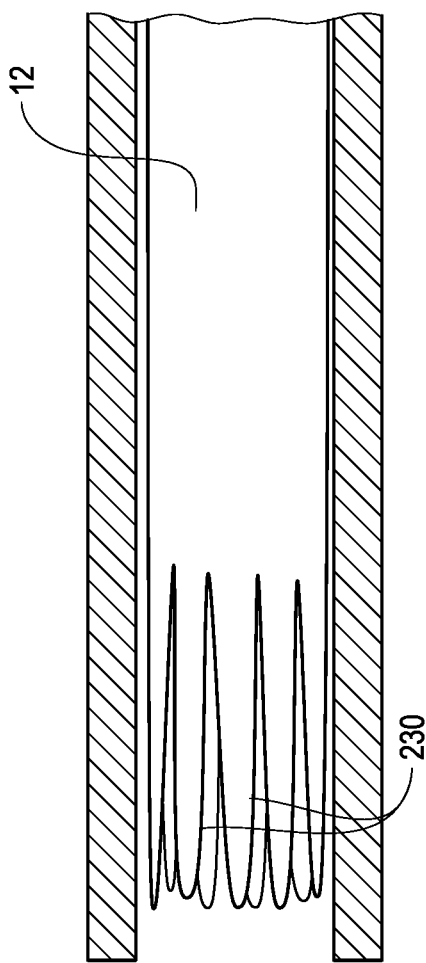
FIG. 11 shows a ureteral stent with fold lines to form an anti-migration feature according to embodiments of the invention.
Figure 12:
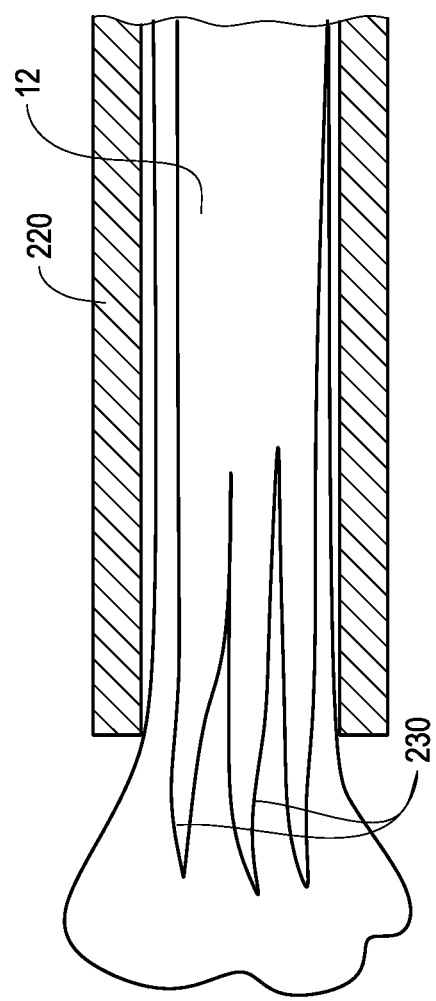
FIG. 12 shows a ureteral stent with fold lines to form an anti-migration feature according to embodiments of the invention.

The tubular body 12 may include one or more fold lines 230 such that the tubular body 12 is configured to collapse upon the fold lines 230 when in a delivery configuration, for example as shown in FIG. 11. The fold lines 230 may include preformed grooves, indentations, or slits to enable the tubular body 12 to collapse and fold upon the fold lines 230. The fold lines 230 in tubular body 12 may be formed into a super-elastic metal mesh, such as one made of nitinol wire, or formed into a polymeric material with self-expanding capabilities. The fold lines 230 cut into tubular body 12 may include multiple layers of mesh, with an outer mesh layer being capable of greater expansion diameters than an inner mesh layer. The inner mesh layer may provide additional anchoring support to the outer mesh layer in the deployment position and may contribute to a superior anchoring capability. The elastic restoring force of the inner mesh layer may provide additional force to secure the ureteral stent 10 in position during deployment. The mesh may be woven or non-woven, collapsible, and self-expanding. The self-expansion may arise from an elastic restoring force to engage the mesh with the surrounding tissue. In some embodiments, the outer mesh layer may expand into a contoured outer shape, being formed into different cross sectional profiles, such as rounded, triangular, square shaped, U-shaped, or wave shaped. It is contemplated that individual wires within the mesh may be shaped with a rounded, triangular, square shaped, U-shaped or wave shaped configuration as illustrated in FIGS. 2B-2F to provide additional anchoring support. As shown in FIGS. 11 and 12, the tubular body 12 may expand radially outward from the fold lines 230 upon removal of the outer sheath 220.

Figure 13:
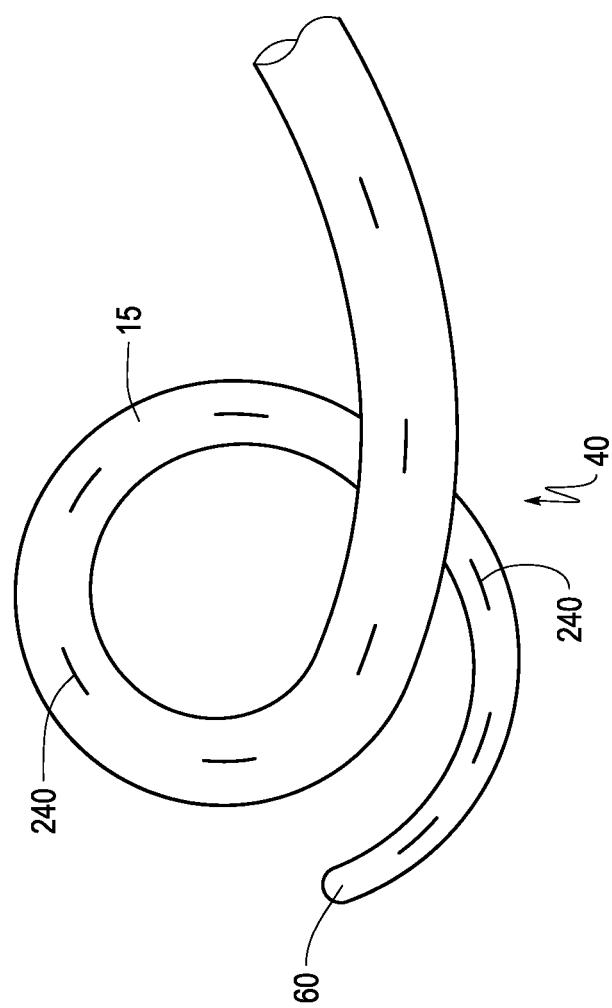
FIG. 13 shows a distal end of a ureteral stent according to embodiments of the invention.

The tubular body 12 may comprise a material suitable to withstand multiple compression and relaxation cycles of a patient's bladder without breaking. Suitable materials include, for example, polymeric materials, such as polyurethane, silicone, PEBAX (polyether block amide), or any biocompatible thermoplastic elastomer. In some embodiments, the distal kidney section 15 of the tubular body 12 may be comprised of a different material than the ureter section 25 and/or the proximal bladder section 20. For example, the distal kidney section 15 may comprise a relatively more flexible material than the ureter section 25 and/or the proximal bladder section 20. A more flexible distal kidney section 15 may allow the distal kidney section 15 to bend and collapse under pressure from a patient's kidney (for example, during urine voiding), and therefore reduce discomfort that is typically associated with a traditional ureteral stent. In some embodiments, the distal kidney section 15 may be thinner and may comprise a relatively stiffer material than the proximal bladder section 20 in order to reduce such discomfort. Additionally or alternatively, the distal kidney section 15 may comprise one or more depressions 240, as shown in FIG. 13. The depressions 240 may provide adequate flexibility to the distal kidney section 15 of tubular body 12 to reduce such discomfort. The depressions 240 may include slits, holes, or indentations in the distal kidney section 15. Alternatively or additionally, the depressions 140 may include a material sufficient to provide such flexibility to the distal kidney section 15. This material may be the same or different from the material of the remainder of the tubular body 12.

The inner and/or outer surfaces of the tubular body 12 may be coated. For example, the inner surface may be coated with a lubricious coating to facilitate the flow of fluid within lumen 14. In some embodiments, the inner surface coating may substantially prevent the growth of biofilm. The outer surface may be coated with, for example, a hydrophilic coating to promote the attachment of the ureteral stent 10 to the ureter wall of a patient.

As shown in FIG. 14, the ureteral stent 10 may be delivered to the ureter 300 of a patient with, for example, outer sheath 220. In this example, the ureteral stent 10 may be positioned within a patient such that the distal end 60 is disposed within the patient's kidney 310 and the proximal bladder section 20 does not enter the patient's bladder 320. The distal kidney section 15 is thus secured within the kidney 310 to prevent and/or reduce antegrade movement of the ureteral stent 10. Furthermore, the proximal bladder section 20 is positioned such that it does not enter the bladder 320 but still provides a secure attachment to the wall of the ureter 300 to prevent and/or reduce retrograde movement of the ureteral stent 10. Thus, ureteral stent 10 may not contact the sensitive bladder tissue in the trigonal region of a patient and thereby reduce pain and discomfort for the patient. In some embodiments, the ureteral stent 10 may be positioned such that the proximal end 50 does not enter the patient's bladder 320. The first and second anti-migration features 30, 40 allow the ureteral stent to remain fixed in place within the patient while the ureteral stent 10 reduces such pain and discomfort. Thus, ureteral stent 10 advantageously provides increased patient comfort.

What is claimed is:

1. A ureteral stent comprising:
   a tubular body defining a lumen and having (i) a distal kidney section to be placed in or near a patient's kidney, (ii) a proximal bladder section to be placed at least partly within the patient's bladder, and (iii) a ureter section between the distal and proximal sections to be placed within the patient's ureter; and
   a first anti-migration feature provided entirely at the proximal bladder section and including one or more projections extending distally and outward from the tubular body, the first anti-migration feature being configured to not enter the patient's bladder.

2. The ureteral stent of claim 1, wherein the first anti-migration feature is retractable.

3. The ureteral stent of claim 1, further comprising:
   a second anti-migration feature provided at the proximal bladder section, the distal kidney section, or both, the second anti-migration feature including at least one of a coiled structure, a mesh structure, and depressions in an outer surface of the tubular body.

4. The ureteral stent of claim 3, wherein the second anti-migration feature includes a coiled structure.

5. The ureteral stent of claim 3, wherein the second anti-migration feature includes depressions in an outer surface of the tubular body.

6. A ureteral stent comprising:
   a tubular body defining a lumen and having (i) a distal kidney section to be placed in or near a patient's kidney, (ii) a proximal bladder section to be placed at least partly within the patient's bladder, and (iii) a ureter section between the distal and proximal sections to be placed within the patient's ureter; and
   a first anti-migration feature including one or more projections extending distally and outward from the tubular body, the first anti-migration feature being configured to be placed entirely within a patient's ureter.

7. The ureteral stent of claim 6, wherein the first anti-migration feature is retractable.

8. The ureteral stent of claim 6, further comprising:
   a second anti-migration feature extending outward from the tubular body and comprising at least one of a coiled structure, a mesh structure, and depressions in an outer surface of the tubular body.

9. The ureteral stent of claim 8, wherein the second anti-migration feature comprises a coiled structure.

10. The ureteral stent of claim 8, wherein the second anti-migration feature comprises depressions in an outer surface of the tubular body.

11. A ureteral stent comprising:
    a tubular body defining a lumen and having (i) a distal kidney section to be placed in or near a patient's kidney, (ii) a proximal bladder section to be placed at least partly within the patient's bladder, and (iii) a ureter section between the distal and proximal sections to be placed within the patient's ureter; and
    a first anti-migration feature disposed on an outer surface of the tubular body, and configured to be placed entirely within a patient's ureter and to reduce movement of the ureteral stent when the ureteral stent is disposed in the patient's ureter,
    wherein the ureteral stent does not include any anti-migration features that would be positioned within the patient's bladder when a distal section of the tubular body is placed in or near the patient's kidney.

12. The ureteral stent of claim 11, wherein the first anti-migration feature includes one or more projections extending outward from the tubular body.

* * * * *